US008987228B2

(12) United States Patent
Fishman

(10) Patent No.: US 8,987,228 B2
(45) Date of Patent: Mar. 24, 2015

(54) PHARMACEUTICAL COMPOSITION INCLUDING AN A3 ADENOSINE RECEPTOR AGONIST 1-DEOOXY-1-[N⁶-(3-IDO-BENZYL)-ADENIN-9-YL]-N-METHYL-β-D-RIBOFURONAMIDE(IB-MECA/CF-101) FOR TREATMENT OF PSORIASIS

(75) Inventor: Pnina Fishman, Herzliya (IL)

(73) Assignee: Can-Fite Biopharma Ltd., Petach Tikva (IL)

( * ) Notice: Subject to any disclaimer, the term of this patent is extended or adjusted under 35 U.S.C. 154(b) by 239 days.

(21) Appl. No.: 13/394,373

(22) PCT Filed: Sep. 6, 2010

(86) PCT No.: PCT/IL2010/000729
§ 371 (c)(1),
(2), (4) Date: Mar. 6, 2012

(87) PCT Pub. No.: WO2011/027348
PCT Pub. Date: Mar. 10, 2011

(65) Prior Publication Data
US 2012/0165284 A1    Jun. 28, 2012

(30) Foreign Application Priority Data
Sep. 6, 2009   (IL) .......................................... 200753

(51) Int. Cl.
*A61K 31/70*     (2006.01)
*C07H 19/16*    (2006.01)
*A61K 31/7076*  (2006.01)

(52) U.S. Cl.
CPC ................................ *A61K 31/7076* (2013.01)
USPC ......................................... 514/46; 536/27.22

(58) Field of Classification Search
CPC ................................................ A61K 31/7076
See application file for complete search history.

(56) References Cited

U.S. PATENT DOCUMENTS

| 6,117,878 | A  | * | 9/2000 | Linden ...................... 514/263.34 |
| 7,732,484 | B2 | * | 6/2010 | Linden et al. ................. 514/447 |
| 2004/0016709 | A1 | | 1/2004 | Felcman et al. |

FOREIGN PATENT DOCUMENTS

| JP | 2008-522182 A | | 6/2008 |
| WO | 2004/045627 | | 6/2004 |
| WO | 2005063246 A1 | | 7/2005 |
| WO | 2006059327 A1 | | 6/2006 |
| WO | 2008-056361 | | 11/2007 |
| WO | 2008056361 A1 | | 5/2008 |
| WO | WO 2008/056361 A1 | * | 5/2008 |
| WO | WO 2009/010967 A1 | * | 1/2009 |
| WO | 2011/027348 | | 3/2011 |

OTHER PUBLICATIONS

Fishman et al., Evidence for involvement of Wnt signaling pathway in IB-MECA mediated suppression of melanoma cells. Oncogene, 2002, pp. 4060-4064, vol. 21.
Fishman et al.,Targeting the A3 adenosine receptor for cancer therapy: inhibition of Prostate carcinoma cell growth by A3AR agonist. Anticancer Res, 2003, pp. 2011-2023, vol. 23.
Madi et al. A3 adenosine receptor activation in melanoma cells: association between receptor fate and tumor growth inhibition. J Bio. Chem., 2003, pp. 42121-42130, vol. 278, No. 43.
G. Ohana et al, Inhibition of primary colon carcinoma growth and liver metastasis by the A3 adenosine receptor agonist CF101. British Journal Cancer, 2003, pp. 1552-1558, vol. 89.
Fishman et al., 2004. An agonist to the A3 adenosine receptor inhibits colon carcinoma growth in mice via modulation of GSK-3β and NF-κB. Oncogene, 2004, pp. 2465-2471, vol. 23, Nature Publishing Group.
Szabo et al. Suppression of macrophage inflammatory protein (MIP)-I production and collagen-induced arthritis by adenosine receptor agonists. British J. Pharmacology, 1998, pp. 379-387, vol. 125.
Mabley et al., 2003. The adenosine A3 receptor agonist, N6-(3-iodobenzyl)-adenosine-5'-N-methyluronamide, is protective in two murine models of colitis. European Journal of Pharmacology, 2003, pp. 323-329, vol. 466.
Baharav et al. The effect of adenosine and the A3 adenosine receptor agonist IB-MECA on joint inflammation and autoimmune diseases models. Inter. J. Mol. Med. 10 (supplement 1), 2002, pp. S 104, abstract 499.
Can-Fite can do phase II, Bioventure View, May 6, 2003.
S.R. Feldman and G.G.Krueger. Psoriasis assessment tools in clinical trials. Dis. 64 (Suppl. II), 2005, pp. ii65-ii68.
A. Ochaion et al. The anti-inflammatory target A3 adenosine receptor is over expressed in rheumatoid arthritis, psoriasis and Crohn's disease. Cellular Immunology, 2009, pp. 115-122, vol. 258.
International Search Report dated Dec. 21, 2010 for PCT/IL10/00729.
Written Opinion mailed Jan. 12, 2011 for PCT/IL10/00729.
Alice B Gottlieb et al, The National Psoriasis Foundation Psoriasis Score System versus the Psoriasis Area Severity Index and Physician's Global Assessment : a comparison; Journal of Drugs in Dermatology / Jun. 2003.

(Continued)

*Primary Examiner* — Lawrence E Crane
(74) *Attorney, Agent, or Firm* — Fleit Gibbons Gutman Bongini & Bianco PL; Martin Fleit; Paul D. Bianco

(57) ABSTRACT

Clinical finding shows that twice daily administrations of 2 mg of 1-deoxy-1-[N⁶-(3-iodobenzyl)-adenin-9-yl]-N-methyl-β-D-ribofuronamide (IB-MECA) (total daily administration of 4 mg) to subjects having moderate to severe psoriasis, was significantly more effective in treatment of the psoriatic plaques than treatment of psoriasis at two administration doses of 1 mg or 4 mg (total daily doses of 2 or 8 mg, respectively). A pharmaceutical composition for the treatment of psoriasis includes as the active ingredient IB-MECA in an amount suitable for a total daily dose administration of about 4 mg. In one preferred embodiment, IB-MECA is administered twice a day to a subject in need of psoriasis treatment, the pharmaceutical composition including an administration dose of 2 mg.

12 Claims, 1 Drawing Sheet

(56) References Cited

OTHER PUBLICATIONS

Jacobson, Medical Chemistry of the A3 Adenosine Receptior; agonists; antagonists and receptor engineering Handb Exp Pharmacol. 2009.

International Preliminary Report on Patentability dated Mar. 6, 2012 for PCT/IL10/00729.

Naldi et al. "Emerging drugs for psoriasis" (2009) vol. 14, n. 1, pp. 145-163, Expert Opinion Emerging Drugs.

Silverman et al "Clinical Evidence for Utilization of the A3 Adenosine Receptor as a Target to Treat Rheumatoid Arthritis" (2008) vol. 35, n. 1, pp. 41-48, The Journal of Rheumatology.

Office Action for JP 2012-527447, Jul. 29, 2014, Notice of Reasons for Rejection.

Jacobson, Medicinal Chemistry o fthe A3 Adnosine Receptor, p. 123-159, 2009 a chapter in "Adenosine Receptors in Health and Disease, " Springer-Verlag, New York, NY, Wilson and Mustafa eds.

* cited by examiner

PHARMACEUTICAL COMPOSITION INCLUDING AN A3 ADENOSINE RECEPTOR AGONIST 1-DEOOXY-1-[N⁶-(3-IDO-BENZYL)-ADENIN-9-YL]-N-METHYL-β-D-RIBOFURONAMIDE(IB-MECA/CF-101) FOR TREATMENT OF PSORIASIS

FIELD OF THE INVENTION

This invention relates to the treatment of psoriasis.

PRIOR ART

The following is a list of prior art which is considered to be pertinent for describing the state of the art in the field of the invention. Acknowledgement of these references herein will at times be made by indicating their number within brackets from the list below.

1. Fishman et al., 2002. Evidence for involvement of Wnt signaling pathway in IB-MECA mediated suppression of melanoma cells. Oncogene., 21:4060-4064 (2002).
2. Fishman et al., 2003. Targeting the A3 adenosine receptor for cancer therapy: inhibition of Prostate carcinoma cell growth by $A_3AR$ agonist. Anticancer Res., 23:2011-2023 (2003).
3. Madi et al., 2003. A3 adenosine receptor activation in melanoma cells: association between receptor fate and tumor growth inhibition. J. Bio. Chem., 278:42121-42130 (2003).
4. Ohana et al., 2003. Inhibition of primary colon carcinoma growth and liver metastasis by the A3 adenosine receptor agonist IB-MECA. British J. Cancer., 89:1552-1558 (2003).
5. Fishman et al., 2004. An agonist to the A3 adenosine receptor inhibits colon carcinoma growth in mice via modulation of GSK-3β and NF-κB. Oncogene, 23:2465-2471 (2004).
6. US Patent Application Publication No. 2004016709 A1.
7. Szabo et al., 1998. Suppression of macrophage inflammatory protein (MIP)-I production and collagen-induced arthritis by adenosine receptor agonists. British J. Pharmacology, 125:379-387 (1998).
8. Mabley et al., 2003. The adenosine $A_3$ receptor agonist, $N^6$-(3-iodobenzyl)-adenosine-5'-N-methyluronamide, is protective in two murine models of colitis. Eur op. J. Pharmacology, 466:323-329 (2003).
9. Baharav et al., 2002. The effect of adenosine and the $A_3$ adenosine receptor agonist IB-MECA on joint inflammation and autoimmune diseases models. Inter. J. MoI. Med. 10 (supplement 1) page S 104, abstract 499 (2002).
10. PCT Application, publication No. WO2005/0063246, entitled "Method for Treatment of Multiple Sclerosis".
12. PCT patent application, publication No. WO2004/045627, entitled "$A_3AR$ agonists for the treatment of inflammatory arthritis".
13. PCT patent application, publication No. WO2008/056361, entitled "A biological marker for psoriasis".
16. Bioventure View, 6 May 2003 "Can-Fite can do phase II".

BACKGROUND OF THE INVENTION

The $A_3$ adenosine receptor, a Gi protein-associated cell surface receptor, was proposed as a target to combat cancer and inflammation. The receptor is highly expressed in various tumor cell types while expression in adjacent normal tissues is relatively low. Activation of the receptor by a specific synthetic agonist induces modulation of downstream signal transduction pathways which include the Wnt and the NF-kB, resulting in tumor growth inhibition (1-5).

In vivo studies have shown that $A_3$ adenosine receptor ($A_3AR$) agonists inhibit the development of colon, prostate and pancreatic carcinomas as well as melanoma and hepatoma. $A_3AR$ agonists were also been shown to act as anti-inflammatory agents by ameliorating the inflammatory process in different experimental autoimmune models such as rheumatoid arthritis, Crohn's disease and multiple sclerosis (6-10).

The $A_3AR$ was found to be highly expressed in inflammatory tissues (synovia and paw) derived from adjuvant (AIA) and collagen induced arthritis experimental models (11). This over expression was reflected in the PBMNC of the animals. Treatment of ALA rats with an $A_3AR$ agonist resulted in disease amelioration and receptor down-regulation. In patients with Rheumatoid arthritis (RA), the receptor was found to be highly expressed in peripheral blood mononuclear cells (PBMNC) (11). Moreover, in a group of RA patients that was treated with an $A_3$ AR agonist, a direct correlation was found between $A_3AR$ expression at baseline and response of the patients to the drug (12).

An increase was also found in the level of $A_3$ adenosine receptor expression in the peripheral blood mononuclear cells (PBMNC) of subjects suffering from psoriasis as compared to the PBMNC of a healthy subject. This finding paved the way for the use of the $A_3AR$ expression level as a means for the diagnosis of a psoriasis state (13)

Psoriasis is a chronic condition. People often experience flares and remissions throughout their life.

There are several forms of psoriasis, and each form has unique characteristics that allow dermatologists to visually identify psoriasis to determine what type, or types, of psoriasis is present. Sometimes a skin biopsy will be performed to confirm the diagnosis. The main types of psoriasis include the following:

Plaque Psoriasis (reddened areas a few inches across covered by silvery scales)

Pustular Psoriasis (blisters of noninfectious pus on red skin)—Arthritic Psoriasis or Psoriatic Arthritis Guttate Psoriasis (small, red spots on the skin)

Inverse or Flexural Psoriasis (shiny, red patches in areas of friction such as in the folds of skin in the groin, the armpits or under the breasts)

Erythroderma Psoriasis (reddening and scaling of most of the skin).

Treatment depends on the severity and type of psoriasis. Some psoriasis is so mild that the person is unaware of the condition. A few develop such severe psoriasis that lesions cover most of the body and hospitalization is required. These represent the extremes. Most cases of psoriasis fall somewhere in between. Psoriasis treatments fall into 3 categories:

Topical (applied to the skin);—Mild to moderate psoriasis;

Phototherapy (light, usually ultraviolet, applied to the skin)—Moderate to severe psoriasis;

Systemic (taken orally or by injection or infusion)—Moderate, severe or disabling psoriasis.

The treatment options can clear psoriasis for a period of time. Each treatment has advantages and disadvantages, and what works for one patient may not be effective for another.

In an article published on the internet (16), it is stated that (1-deoxy-1-[$N^6$-(3-iodobenzyl)-adenin-9-yl]-N-methyl-β-D-ribofuronamide, IB-MECA, an $A_3AR$ agonist) could be applicable in indications such as inflammatory bowel disease and psoriasis.

SUMMARY OF THE INVENTION

The present invention is based on the clinical finding that oral administration of IB-MECA to subjects having moderate to severe psoriasis, in daily dose of 4 mg (twice daily administration of 2 mg) was significantly more effective in treatment of the psoriatic plaques than treatment of psoriasis at daily doses of 2 mg or 8 mg.

Thus, the present disclosure provides a pharmaceutical composition, e.g. in dosage form, for the treatment of psoriasis comprising as an active ingredient 1-[$N^6$-(3-iodobenzyl)-adenin-9-yl]-β-D-ribofuronamide (IB-MECA) in an amount suitable for a total daily dose of about 4 mg.

The term "about" should be understood to encompass a dose that is within a range of 33% less or 33% more ("±33%"), preferably ±25%, particularly ±20%, ±15%, and even ±10% than the indicated dose.

The term "daily dose" should be understood to encompass the amount of the active ingredient, namely, IB-MECA being administered per day to the subject in need thereof. The daily dose may encompass a single daily administration or more than one administrations per day, as long as the total amount of IB-MECA received by the subject per day is about 4 mg.

In line with the above, the pharmaceutical composition may formulated for a single daily administration, in which case the amount of IB-MECA in the composition is about 4 mg, or for administration twice a day, in which case the amount of IB-MECA is about 2 mg. Similarly, the composition may be formulated for 3- or 4-times daily administration in which case the dosage form will comprise, respectively, about 1.33 and 1 mg of IB-MECA.

The present disclosure also provides IB-MECA for use in the treatment of psoriasis, the IB-MECA being administered to a subject having psoriasis in a total daily dose of about 4 mg.

Further provided by the present disclosure is a method of treatment of psoriasis, the method comprising administering to a subject having psoriasis IB-MECA at a total daily dose of about 4 mg.

Finally, provided by the present disclosure is a package comprising IB-MECA or a pharmaceutical composition comprising IB-MECA and instructions for use of IB-MECA or the composition comprising the same for the treatment of a patient having psoriasis with a 4 mg daily amount of IB-MECA.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
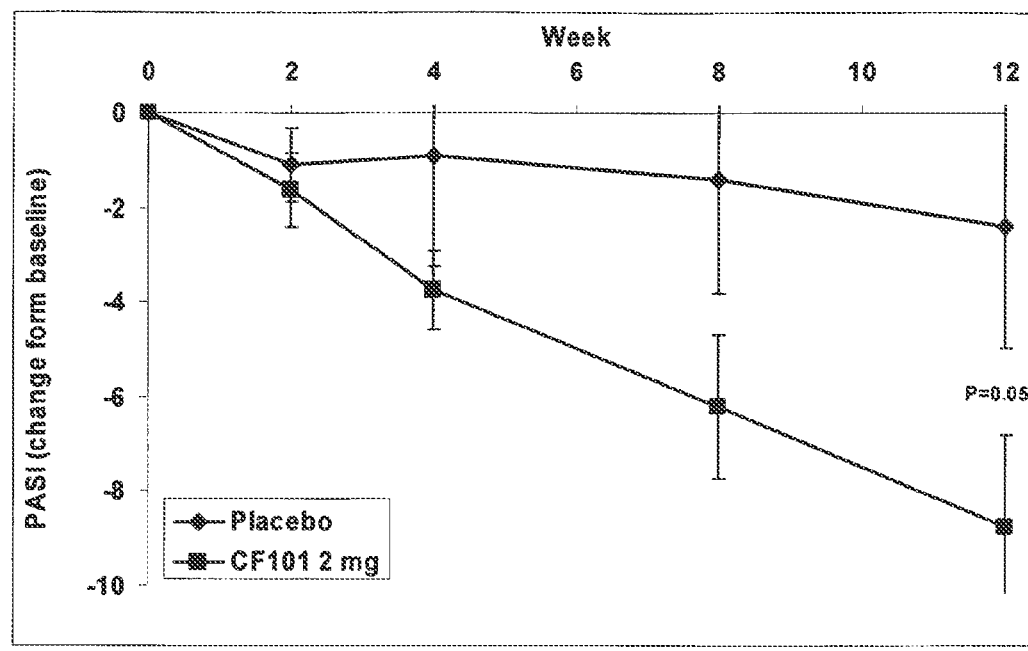
FIG. 1 is a graph showing the change in the Psoriasis Area and Severity Index (PASI) score from baseline over the study period of the 2 mg IB-MECA group (CF101) versus placebo.

The present invention is based on clinical trials in psoriasis patients where the effect of IB-MECA in ameliorating disease symptoms in psoriasis patients was tested. The study results demonstrated a marked effect of 2 mg dose of IB-MECA, administered twice daily (namely a total daily dose of 4 mg) in ameliorating disease manifestation in these patients. Moreover the results demonstrated that a daily dose of 4 mg is superior to a lower daily dose of 2 mg or a higher dose of 8 mg.

In the context of the present disclosure the term "psoriasis" encompass any form of psoriasis including, without being limited thereto, plaque psoriasis; pustular psoriasis (including arthritic psoriasis or psoriatic arthritis); Guttate psoriasis; inverse or flexural psoriasis; erythroderma psoriasis. Further, in the context of the present invention, when referring to "psoriasis" it is meant to include any degree of psoriasis, including, mild, moderate and severe psoriasis.

In the context of the present disclosure the term "treatment" includes any improvement in one or more objective parameters that are used to assess a psoriatic state (severity) in clinical trials, namely redness, thickness and scalliness of psoriatic lesions. Based on these parameters, several tools for assessing the effectiveness of treatment of psoriasis have been developed. The assessment tools include traditional assessment tools such as the Psoriasis Area and Severity Index (PASI), the Physician Global Assessment (PGA), as well as more recent assessment tools, such as the National Psoriasis Foundation Psoriasis Score (NPF-PS), the Physical Static Global Assessment (PSGA) and Overall Lesion Assessment (OLA) [S. R. Feldman and G. G. Krueger *Psoriasis assessment tools in clinical trials*, Ann Rheum. Dis. 64 (Suppl. II):ii65-ii68 (2005)].

PASI and PGA are the two most commonly used tools in assessing psoriasis activity and in following clinical response to treatment. The PASI assessment tool evaluates the degree of erythema, thickness and scaling of psoriatic plaques and estimates the extent of involvement of each of these components in four separate body areas (head, trunk, upper and lower extremities). The PASI composite score ranging from 0-72. The PGA assessment tool is a six point score that summarizes the overall erythema, scaling, and thickness and the extend of plaques relative to a baseline assessment, the scores including worse, poor (0-24%), fair (25-49%), good (50-74%), excellent (75-99%) and cleared (100%). [Alice B Gottlieb et al. *The National Psoriasis Foundation Psoriasis Score System versus the Psoriasis Area Severity Index and Physician's Glogal Assessment: a comparison*, Journal of Drugs in Dermatology June 2003].

The present invention provides a pharmaceutical composition comprising as active ingredient IB-MECA, the use of IB-MECA in treatment and a method for treatment of psoriasis, the composition, use and method being characterized in that the active ingredient, i.e. IB-MECA is administered to achieve a total daily dose of about 4 mg.

In a preferred embodiment, the active ingredient, namely, IB-MECA, is formulated in a form suitable for oral administration. However, in some embodiments the composition may be formulated for nasal administration, may be in the form of an inhaled formulation, may in the form of a suppository or may even be formulated for parenteral administration.

Oral administration, in the context of the present invention, includes any one of (a) liquid solutions, such as an effective amount of IB-MECA dissolved in diluents, such as water, saline or even orange juice; (b) solid and semi solid forms; (c) powders; (d) suspensions in an appropriate liquid; and (e) suitable emulsions. IB-MECA will typically be formulated in a dosage for suitable to achieve the desired daily dose of 4 mg.

Liquid forms may include diluents, such as water and alcohols, for example, ethanol, benzyl alcohol, and the polyethylene alcohols, either with or without the addition of a pharmaceutically acceptable surfactant, suspending agent, or emulsifying agent.

Solid forms, which are a preferred administration form in the context of the invention, may include, without being limited thereto, pills, tablets, including immediate and modified (controlled) release tablets, uncoated and coated tablets (including enteric coating), chewable tablets, bi or multi layer tablets; pellets; capsules, including soft gelatin gel capsules and hard shelled gelatin capsules; powders including granules and oral powders for reconstitution, lozenges, cachets.

The capsules may include, for example, surfactants, lubricants, and inert fillers, such as lactose, sucrose, calcium phosphate, and corn starch. The tablets may include one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. The lozenges may comprise IB-MECA in a flavor, such as sucrose and acacia or tragacanth, as well as pastilles comprising IB-MECA in an inert base, such as gelatin and glycerin, or sucrose and acacia, emulsions, gels, and the like containing, in addition to IB-MECA, such carriers as are known in the art.

The pharmaceutical composition further comprises at least one pharmaceutically acceptable excipient so as to facilitate oral delivery of IB-MECA.

In one embodiment, the pharmaceutical composition is in the form of a tablet. A tablet may be made by compression or molding, optionally with one or more of said excipients. Compressed tablets may be prepared by compressing in a suitable machine IB-MECA in a free-flowing form, e.g., a powder or granules, optionally mixed with the excipient(s), e.g., binders, lubricants, inert diluents, surface active or dispersing agents. Molded tablets may be made by molding in a suitable machine, a mixture of the powdered IB-MECA with any suitable carrier.

In one embodiment, the tablet includes the components shown Table 1 provided hereinafter in the description of a non-limiting example.

A person versed in the art of pharmacy and formulation technologies of pharmaceutical ingredients will be able to devise a myriad of different formulations for oral or other form of administration.

In accordance with the present disclosure, IB-MECA may be administered once, twice or several times a day. In one embodiment, IB-MECA is administered once a day, the dosage form including about 4 mg of IB-MECA. In another embodiment, IB-MECA is administered twice a day, each administration dosage form including about 2 mg of IB-MECA (to achieve the total daily amount of 4 mg).

The present disclosure also provide the use of IB-MECA in the treatment or in the preparation of a pharmaceutical composition for the treatment of psoriasis, the administration dose being formulated in a form suitable for a daily administration of about 4 mg of IB-MECA.

Finally, the present disclosure provides IB-MECA for use in the treatment of psoriasis, said IB-MECA being administered to a subject having psoriasis in a daily dose amount of about 4 mg.

DESCRIPTION OF A NON-LIMITING EXAMPLE

A Phase 2, multi-center, randomized, double-blind, placebo-controlled clinical study was conducted in adult males and females, with ages of 18 to 70 years, with a diagnosis of moderate-to-severe chronic plaque psoriasis.

Inclusion and exclusion criteria included the following:

Inclusion Criteria:
  Male or female, 18 to 70 years of age, inclusive;
  Diagnosis of moderate-to-severe chronic plaque-type psoriasis with body surface area involvement ≥10%, as judged by the Investigator;
  Duration of psoriasis of at least 6 months;
  PASI score ≥10;
  Body weight ≤100 kg;
  Candidate for systemic treatment or phototherapy for psoriasis;
  Electrocardiogram (ECG) is normal or shows abnormalities which, in the judgment of the Investigator, are not clinically significant;
  Females of child-bearing potential must have a negative serum pregnancy test at screening;
  Females of child-bearing potential must be willing to use 2 methods of contraception deemed adequate by the Investigator (for example oral contraceptive pills plus a barrier method) to be eligible for, and continue participation in, the study;
  Ability to complete the study in compliance with the protocol; and
  Ability to understand and provide written informed consent.

Exclusion Criteria:
  Erythrodermic, guttate, palmar, plantar, or generalized pustular psoriasis;
  Treatment with systemic retinoids, corticosteroids, or immunosuppressants (e.g., methotrexate, cyclosporine) within 6 weeks of the Baseline visit;
  Treatment with high potency topical corticosteroids (Class I-III), keratolytics, or coal tar (other than on the scalp, palms, groin, and/or soles) within 2 weeks of the Baseline visit;
  UV or Dead Sea therapy within 4 weeks of the Baseline visit, or anticipated need for either of these therapies during the study period;
  Treatment with a biological agent (including etanercept, adalimumab, efalizumab, infliximab, or alefacept) within a period of time equal to 5 times its circulating half-life, or 30 days, whichever is longer, prior to the Baseline visit;
  History of poor clinical response to methotrexate after an adequate regimen and duration of treatment;
  Treatment with systemic nonsteroidal anti-inflammatory drugs, beta-blockers, lithium, hydroxychloroquine, chloroquine, or systemic terbinafine within 2 weeks of the Baseline visit, or anticipated need for such drugs during the study period;
  Presence or history of uncontrolled asthma;
  Presence or history of uncontrolled arterial hypertension or symptomatic hypotension;
  Significant cardiac arrhythmia or conduction block, congestive heart failure (New York Heart Association Class 3-4), or any other evidence of clinically significant heart disease or clinically significant findings on screening ECG;
  Hemoglobin level <9.0 gm/L;
  Platelet count <125,000/mm$^3$;
  White blood cell (WBC) count <3500/mm$^3$;
  Serum creatinine level greater than 1.5 times the laboratory's upper limit of normal;
  Liver aminotransferase levels greater than 2 times the laboratory's upper limit of normal;
  Known or suspected immunodeficiency or human immunodeficiency virus positivity;
  Known active or untreated tuberculosis;
  Known infection with hepatitis B or C;
  Pregnancy, planned pregnancy, lactation, or inadequate contraception as judged by the Investigator;
  History of drug or alcohol dependence;
  History of serious drug or iodine allergy or sensitivity;
  Previous receipt of IB-MECA;
  History of malignancy within the past 5 years (excluding basal cell carcinoma of the skin and ≤3 cutaneous squamous cell carcinomas, all of which have been completely excised);
  Significant acute or chronic medical or psychiatric illness that, in the judgment of the Investigator, could compromise patient safety, limit the patient's ability to complete the study, and/or compromise the objectives of the study;

Participation in another investigational drug or vaccine trial concurrently or within 30 days; or within 5 half lives of a biological investigational product, whichever is longer;

Other conditions which would confound the study evaluations or endanger the safety of the patient.

Eligible patients were randomly assigned to receive either placebo or a clinical grade 11-deoxy-1-[N$^6$-(3-iodobenzyl)-adenin-9-yl]-N-methyl-β-D-ribofuronamide, IB-MECA (code-named by the study sponsor, Can-Fite Biopharma, the Assignee of this application, as "CF101") at doses of 1 mg, 2 mg and 4 mg, taken orally twice daily (namely, total daily doses of 2 mg, 4 mg and 8 mg, respectively). IB-MECA was formulated in a tablet formulation as detailed in Table 1 below. Patients were instructed to take the formulation on an empty stomach. The study duration was 12 weeks.

TABLE 1

IB-MECA formulation

| | Ingredient | 1 mg Tablet | 2.0 mg Tablet | 4.0 mg Tablet |
|---|---|---|---|---|
| Intragranular | IB-MECA Bulk Drug Substance | 0.1000 | 1.000 | 4.000 |
| | Pregelatinized Starch | 10.00 | 10.00 | 10.00 |
| | Croscarmellose Sodium | 2.000 | 2.000 | 2.000 |
| | Lactose Monohydrate 310 | 64.25 | 63.25 | 61.25 |
| | Microcrystalline Cellulose | 20.00 | 20.00 | 20.00 |
| Extragranular | Croscarmellose Sodium | 2.000 | 2.000 | 2.000 |
| | Magnesium Stearate | 0.7500 | 0.7500 | 0.7500 |
| | Total | 100.00 | 100.00 | 100.00 |
| Coating | Opadry White | 3.000 | 3.000 | 3.000 |
| | Total | 103.0 | 103.0 | 103.0 |

The study was carried out in cohorts:
Cohort 1: 1 mg IB-MECA or placebo.
Cohort 2: 2 mg IB-MECA or placebo.
Cohort 3: 4 mg IB-MECA or placebo.

Within each cohort, patients were randomly assigned to either IB-MECA or placebo in a 3:1 ratio.

Disease was assessed using the Psoriasis Area and Severity Index (PASI).

Sixty two (62) patients were evaluated that belonged ton the following treatment groups (administration twice a day):
Placebo: 15 patients
One mg IB-MECA: 14 patients
Two mg IB-MECA: 17 patients
Four mg IB-MECA: 16 patients.

Figure 2:
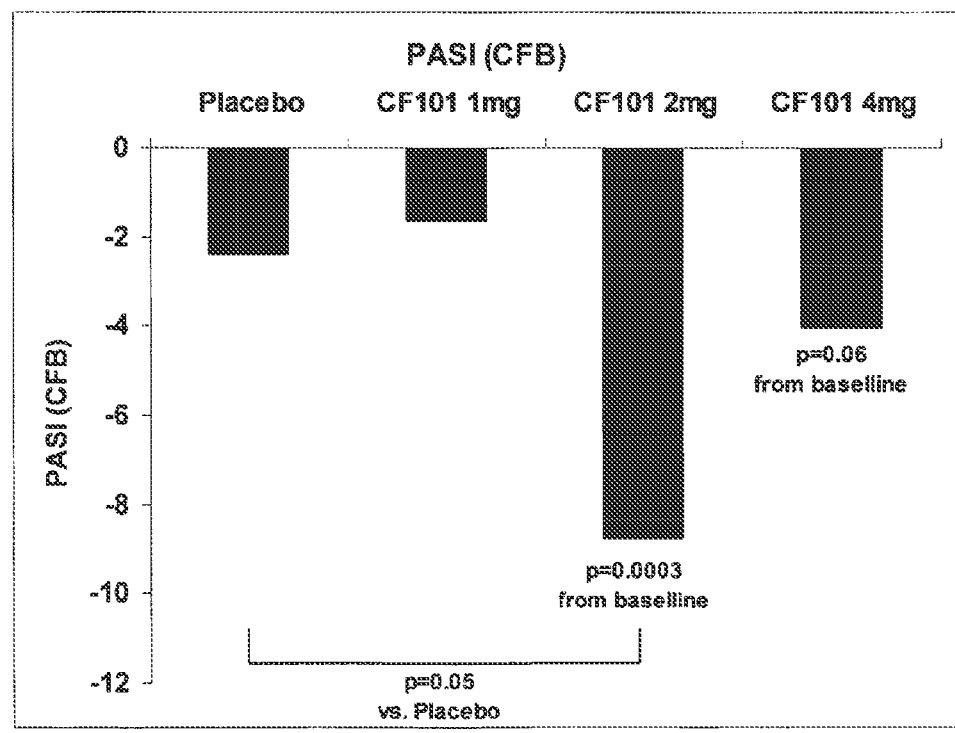
FIG. 2 is a histogram showing the difference between three doses of IB-MECA (1 mg, 2 mg and 4 mg) in the change in the PASI score from baseline over the study period.

The results are shown in FIGS. 1 and 2.

FIG. 1 shows the change in the PASI score from baseline over the study period of the total 4 mg IB-MECA group (2 mg administered twice daily) versus placebo, demonstrating a continuous improvement in the patients' condition throughout the course of the study in the 4 mg IB-MECA group without or very little change in the placebo group.

As can be seen in FIG. 2, the 2 mg dose group (total of 4 mg/day) of IB-MECA had a profound and previously unexpected advantage in generating a considerably greater response over the two other tested dose groups.

The invention claimed is:

1. A method for treating psoriasis in a subject in need thereof, comprising:
providing a total daily dose of about 4 mg of 1-deoxy-1-[N$^6$-(3-iodobenzyl)-adenin-9-yl]-N-methyl-β-D-ribofuronamide (IB-MECA); and
administering the dose of IB-MECA to the subject twice daily in an amount of about 2 mg per dose, whereby psoriasis is treated in the subject.

2. The method according to claim 1, wherein the IB-MECA is administered orally to the subject.

3. The method according to claim 1, wherein the IB-MECA is in a form selected from the group consisting of liquids, suspensions, emulsions, semi-solids, pills, tablets, capsules, pellets, powders, lozenges, and cachets.

4. The method according to claim 1, wherein the daily dose is a composition further comprising one or more of surfactants, lubricants, inert fillers, excipients, diluents, buffering agents, disintegrating agents, colorants, moistening agents, preservatives, flavoring agents, and pharmacologically-compatible carriers.

5. A method for treating psoriatic plaques in a subject in need thereof, comprising:
providing a total daily dose of about 4 mg of 1-deoxy-1-[N$^6$-(3-iodobenzyl)-adenin-9-yl]-N-methyl-β-D-ribofuronamide (IB-MECA); and
administering the dose of IB-MECA to the subject twice daily in an amount of about 2 mg per dose, whereby the psoriatic plaques are treated in the subject.

6. The method according to claim 5, wherein the IB-MECA is administered orally to the subject.

7. The method according to claim 6, wherein the IB-MECA is in a form selected from the group consisting of liquids, suspensions, emulsions, semi-solids, pills, tablets, capsules, pellets, powders, lozenges, and cachets.

8. The method according to claim 5, wherein the daily dose is a composition further comprising one or more of surfactants, lubricants, inert fillers, excipients, diluents, buffering agents, disintegrating agents, colorants, moistening agents, preservatives, flavoring agents, and pharmacologically-compatible carriers.

9. A method for ameliorating symptoms of psoriasis in a subject in need thereof, comprising:
providing a total daily dose of about 4 mg of 1-deoxy-1-[N$^6$-(3-iodobenzyl)-adenin-9-yl]-N-methyl-β-D-ribofuronamide (IB-MECA); and
administering the dose of IB-MECA to the subject twice daily in an amount of about 2 mg per dose, whereby the symptoms of psoriasis are ameliorated in the subject.

10. The method according to claim 9, wherein the IB-MECA is administered orally to the subject.

11. The method according to claim 10, wherein the IB-MECA is in a form selected from the group consisting of liquids, suspensions, emulsions, semi-solids, pills, tablets, capsules, pellets, powders, lozenges, and cachets.

12. The method according to claim 9, wherein the daily dose is a composition further comprising one or more of surfactants, lubricants, inert fillers, excipients, diluents, buffering agents, disintegrating agents, colorants, moistening agents, preservatives, flavoring agents, and pharmacologically-compatible carriers.

* * * * *